United States Patent
Delack

(10) Patent No.: US 8,211,872 B1
(45) Date of Patent: Jul. 3, 2012

(54) METHOD AND COMPOSITION FOR TREATMENT OF MULTIPLE SCLEROSIS AND RELATED NEURODEGENERATIVE CONDITIONS

(75) Inventor: Elaine A. Delack, Stanwood, WA (US)

(73) Assignee: MedDEV, Inc., Bellingham, WA (US)

( * ) Notice: Subject to any disclaimer, the term of this patent is extended or adjusted under 35 U.S.C. 154(b) by 862 days.

(21) Appl. No.: 12/290,036

(22) Filed: Oct. 24, 2008

Related U.S. Application Data

(60) Provisional application No. 61/000,314, filed on Oct. 24, 2007.

(51) Int. Cl.
*A01N 57/00* (2006.01)
*A61K 31/675* (2006.01)

(52) U.S. Cl. ............. 514/94; 514/92; 514/114; 514/119

(58) Field of Classification Search ...................... 514/94
See application file for complete search history.

(56) References Cited

U.S. PATENT DOCUMENTS

| | | |
|---|---|---|
| 6,277,402 B1 | 8/2001 | DeLack |
| 7,232,830 B2 | 6/2007 | DeLack |

*Primary Examiner* — Sreeni Padmanabhan
*Assistant Examiner* — Timothy E Betton
(74) *Attorney, Agent, or Firm* — Todd N. Hathaway

(57) ABSTRACT

A method for treating the symptoms of multiple sclerosis and related neurodegenerative conditions, using a histamine compound that is methylated in vitro prior to being introduced into the body of the patient. The histamine compound is suitably histamine diphosphate, and may be methylated in vitro by mixing in combination with at least one thiol compound in the presence of at least one methyl group donor compound. The thiol compound is suitably L-reduced glutathione and the methyl group donor is suitably betaine hydrochloride. The compounds are mixed vigorous in an acid environment, to create a shearing force that facilitates exchange of the methyl group from the donor compound to the histamine diphosphate. The resulting methylated histamine compound is suitably administered to the patient by transdermal application. The method also provides a medicament for treatment the symptoms of multiple sclerosis and related neurodegenerative conditions, and a method for preparation of such a medicament.

15 Claims, 1 Drawing Sheet

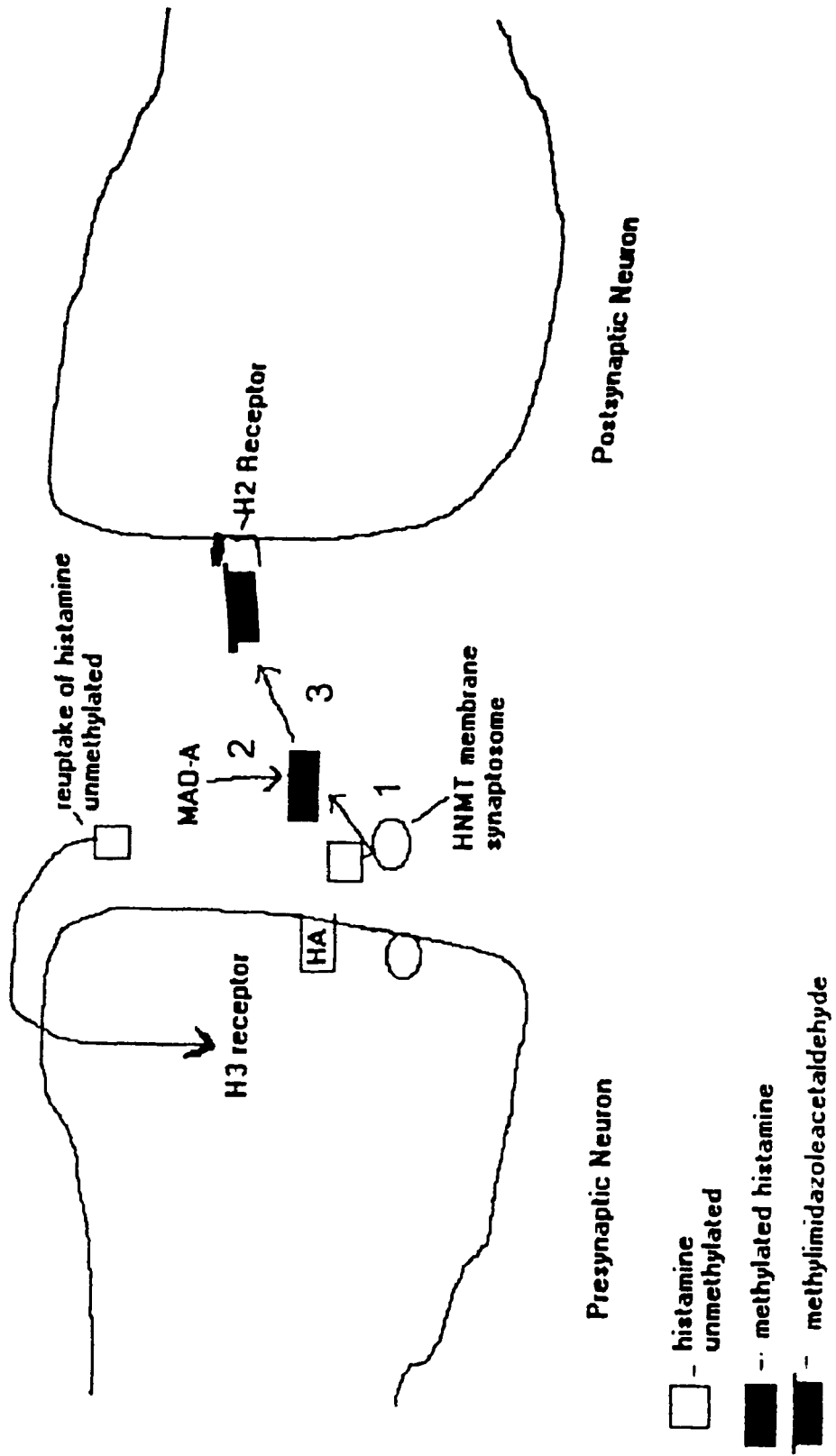

METHOD AND COMPOSITION FOR TREATMENT OF MULTIPLE SCLEROSIS AND RELATED NEURODEGENERATIVE CONDITIONS

RELATED APPLICATIONS

This application claims the benefit of U.S. Provisional Patent Application Ser. No. 61/000,314 filed on Oct. 24, 2007.

BACKGROUND a. Field of the Invention

The present invention relates generally to methods for the treatment of neurological conditions, and, more particularly, to a method for alleviating/controlling symptoms associated with neurodegeneration and similar conditions stemming from multiple sclerosis, autoimmune diseases, aging, and other causes, by administration of a compound effective to increase synaptic methylation of histamine without reliance on endogenous histamine N-methyltransferase (HMT) activity or exogenous administration of HMT.

b. Related Art

Neurodegenerative conditions, which include diseases of autoimmunity, strike an increasingly large number of individuals each year, and for many of these conditions conventional treatments offer little in the way of true relief. A particularly widespread and well-known example is multiple sclerosis (referred to from time-to-time hereinafter as "MS").

In some instances, the neurodegenerative conditions are more or less specifically associated with a particular disease, such as multiple sclerosis, while in other instances the conditions are associated more generally with aging or some other condition or process of the body, such as a genetic disorder or an autoimmune disease, fibromyalgia, for example. As a group, however, these conditions are characterized by weakness and impaired physical functions, and, sometimes, impaired mental functions as well. Debilitation is often progressive, and, as stated, conventional treatments and therapies have been limited in their success.

For purposes of illustration, the invention will be described below largely in the context of multiple sclerosis, which is a condition to which the invention has particular applicability; however, it will be understood that the present invention is applicable to a range of neurodegenerative conditions such as those noted above, including autoimmune diseases, fibromyalgia and others, and therefore is not limited in scope to the treatment of multiple sclerosis alone.

As is known, multiple sclerosis is a chronic degenerative disease of the central nervous system, characterized by demyelination of the nerve axons. Symptoms include varying degrees of fatigue, numbness, tremors/muscle spasms and paralysis, coupled with a heightened susceptibility to heat and other environmental stressors. Currently, approximately 4,000,000 people worldwide have been diagnosed as having multiple sclerosis. Onset of the disease usually occurs between 20 and 40 years of age.

It is recognized that MS occurs in at least two general types, i.e. "remissive-relapsive", in which acute exacerbations are separated by periods of partial recovery, and "chronic-progressive", in which the symptoms continue generally unrelieved and there is a progressive deterioration of the patient's condition that may eventually result in total debilitation.

Efforts at treatment of MS have heretofore concentrated almost entirely on the body's autoimmune response system. The prevailing theory has been that some agent causes the myelin sheath to be attacked by the immune system, resulting in destruction of the myelin and creation of lesions. It is also believed that certain viruses may play a role in causing or precipitating MS: In particular, the measles virus may be involved in the disease, in that studies have not only found that people suffering from MS almost invariably possess the measles antigen, but also that MS patients generally have higher than normal levels of measles antibodies in their serum and cerebrospinal fluid. One theory has been that the measles or other virus triggers the T-cells to attack and destroy the myelin sheath.

Proceeding on the theory that MS is the result of an autoimmune response triggered by measles or another virus, most conventional treatment techniques have involved the use of Betaseron, Avonex, Rebif and/or other antiviral substances, generally referred to collectively as "Interferon". The intended purpose of these materials is to impede the RNA-DNA transcription process in the T-cells, which is believed to be triggered by the virus attacking the myelin. While interferon has demonstrated some positive results when treating remissive-relapsive type MS, it has proven almost entirely ineffective against the chronic-progressive type.

Another treatment method, that has yielded modest success in alleviating the symptoms associated with multiple sclerosis, is the transdermal administration of an H2 agonist such as histamine diphosphate, together with a phosphodiesterase inhibitor such as caffeine citrate to stimulate production of cyclic AMP at a level which is sufficient to maintain myelin against undergoing self-degeneration. This treatment is described in U.S. Pat. No. 6,277,402, the inventor therein being the same as in the present matter. A related treatment, again by the same inventor described in U.S. Publication No. 20030113309, involves administering monoamine oxidase-A or monoamine oxidase-A agonists to increase the neuronal metabolism of histamine to a histamine H2 agonist.

As is described in the above references, histamine in the neurons is metabolized by histamine N-methyltransferase (HMT) into tele-methylhistamine (N-tau-methylhistamine). Tele-methylhistamine is then metabolized by monoamine oxidase-A into 4-methylhistamine (histamine methylimidazoleacetaldehyde) which is an H2 agonist. HMT is considered to be the rate-limiting enzyme in this metabolic pathway of metabolizing histamine into histamine methylimidazoleacetaldehyde, in that the histamine must be methylated before the monoamine oxidase-A can metabolize it into the H2 agonist. Research shows that HMT level of activity is regulated by inheritance (Preuss et al, 1998). Thus, the degree of effectiveness of the treatment disclosed in U.S. Pat. No. 6,277,402 could be dependent on the endogenous level of activity of HMT that in turn may be determined by inheritance.

Accordingly, there is a need for a treatment for neurodegenerative conditions such as those described above, in which neuronal metabolism of histamine to a histamine H2 agonist is enhanced without relying on the patient's potentially impaired endogenous HMT activity.

SUMMARY OF THE INVENTION

The present invention provides a method in which histamine diphosphate is methylated in vitro prior to its introduction to the body, thereby bypassing the need for endogenous HMT to methylate the histamine into tele-methylhistamine. As a result, the method produces adequate levels of the H2 agonist to achieve increased effectiveness in alleviating the symptoms associated with multiple sclerosis and other related neurodegenerative conditions.

Broadly, the method comprises methylating histamine in vitro, prior to or at the time of administration to the patient. The step of methylating the histamine in vitro may comprise combining histamine diphosphate with at least one thiol, in the presence of a suitable methyl donor. The thiol may be selected from the group consisting of N-acetylcystiene, glutathiones, L-reduced glutathione, and combinations thereof. The methyl donor may be selected from the group consisting of betaine hydrochloride, S-adenosylmethionine, methionine, and combinations thereof. The thiol may preferably be L-reduced glutathione, and the methyl donor may preferably be betaine hydrochloride. The methylation may be performed in an acid environment, with vigorous mixing under pressure to facilitate exchange of the methyl group to the histamine.

The betaine hydrochloride may be included in an amount in the range from about 15 gm to about 30 gm per each 500 gm of the histamine diphosphate, with the L-reduced glutathione being included in an amount in the range from about 1 gm to about 10 gm per each 15 gm-30 gm of the betaine hydrochloride. The acid environment in which the compounds are mixed preferably has a pH less than about 3.0.

The step of administering the compound to the client may comprise administering an effective amount of the methylated histamine compound by transdermal application. The step of administering an effective amount of the methylated histamine compound by transdermal application may comprise administering the compound by transdermal application twice daily, in the amount in the range from about 0.2 mg to about 5.5 mg per dose, a dose of about 1.65 mg being generally suitable.

The invention further provides a compostion for treating symptoms associated with multiple sclerosis and other, related neurodegenerative conditions, comprising a histamine that is methylated in vitro prior to introduction into the body of the patient. The methylated histamine compound is suitably methylated histamine diphosphate. The compound may comprise a mixture of histamine diphosphate, at least one thiol compound, and a suitable methyl donor compound. The thiol compound may be selected form the group consisting of N-acetylcysteine, glutathiones, L-reduced glutathione, and combinations thereof, with L-reduced glutathione being preferred. The methyl donor may be selected from the group consisting of betaine hydrochloride, S-adenosylmethionine, methionine, and combinations thereof, with betaine hydrochloride being preferred.

The invention further provides a method for preparation of a composition for treating the symptoms of multiple sclerosis and related neurodegenerative conditions, comprising the steps of (a) providing a histamine compound, and (b) methylating the histamine compound in vitro to form a methylated histamine compound for introduction into the body of a patient. The histamine compound is suitably histamine diphosphate, and the step of methylating the histamine compound in vitro may comprise combining the histamine diphosphate with at least one thiol compound in the presence of at least one methyl group donor compound. The at least one thiol compound may be selected from the group consisting of N-acetylcystiene, glutathiones, L-reduced glutathione, and combinations thereof. The methyl group donor compound may be selected from the group consisting of betaine hydrochloride, S-adenosylmethionine, methionine, and combinations thereof. The thiol compound is preferably L-reduced glutathione, and the methyl group donor compound is preferably betaine hydrochloride.

The step of methylating the histamine compound in vitro may further comprise the step of vigorously mixing the histamine diphosphate, the L-reduced glutathione, and the betaine hydrochloride under pressure in an acid environment so as to create a shearing force that facilitates exchange of the methyl group from the methyl group donor compound to the histamine diphosphate. The acid environment preferably has a pH less than about 3.0.

The betaine hydrochloride may be included in an amount in the range from about 50 gm to about 30 gm per each 500 gm of the histamine diphosphate, and the L-reduced glutathione may be included in an amount in the range from about 1 gm to about 10 gm per each 15 gm-30 gm of the betaine hydrochloride.

The step of mixing the compounds may further comprise vigorously mixing the compounds in the acid environment until a thickened paste is formed. The method may further comprise the steps of placing the thickened paste in at least one mould, and allowing the thickened paste to harden in the mould.

These and other features and advantages of the present invention will be more fully appreciated from a reading of the following detailed description with referenced to the accompanying drawings.

BRIEF DESCRIPTION OF THE DRAWINGS

FIG. 1 is a schematic representation of a nerve synapse, showing the interaction of monoamine oxidase-A, methylated and unmethylated histamine, methylimidazoleacetaldehyde and HNMT membrane synaptosome, with respect to the H3 and H2 receptors of the pre-synaptic and post-synaptic neurons.

DETAILED DESCRIPTION

The present invention provides a method and composition for treatment of MS and other neurodegenerative conditions, i.e. autoimmune diseases, fribromyalgia, and also of certain related conditions and symptoms usually associated with aging, by increasing neuronal metabolism of histamine in order to produce increased histamine H2 levels. The increased histamine metabolism is achieved by methylating the histamine in vitro prior to administering it in vivo, so as to bypass the need for adequate endogenous histamine N-methyltransferase (HMT) activity, to produce the histamine H2 levels.

a. Hypothesis

While not intended to be binding with respect to the practice or scope of the present inventions, a hypothesis has been developed which explains the results and that have been observed in connection with the treatment described herein.

As is set forth in the inventor's prior U.S. Pat. No. 6,277, 402, it is believed that the neurodegenerative diseases and conditions to which the present invention is directed stem from or relate to inadequate production of histamine H2.

Histamine is produced in the neurons from the decarboxylation of L-histidine by Histidine decarboxylase. Histamine in the central nervous system is then methylated by Histamine N-methyltransferase (HMT) to produce Tele-methylhistamine (N-tau-methylhistamine). Tele-methylhistamine is then metabolized by Monoamine oxidase-A (MAO-A) to produce the H2 agonist, Tele-methylimidazoleacetaldehyde (Oishi, "Turnover of brain histamine and its changes by various drugs", Nippon Yakurigaku Zasshi, November 1988, 92:271-81). To illustrate this, Table A shows the sequential steps in the production and metabolism of histamine to yield histamine H2 in the central nervous system.

TABLE A

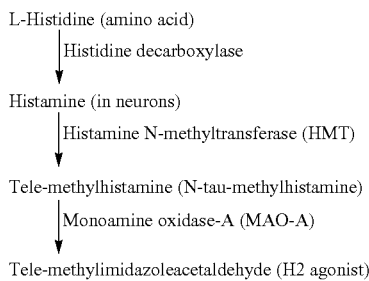

L-Histidine (amino acid)
↓ Histidine decarboxylase
Histamine (in neurons)
↓ Histamine N-methyltransferase (HMT)
Tele-methylhistamine (N-tau-methylhistamine)
↓ Monoamine oxidase-A (MAO-A)
Tele-methylimidazoleacetaldehyde (H2 agonist)

The presynaptic nerve releases histamine and HMT into the nerve synapse. In the nerve synapse the histamine comes in contact with the membrane of the HMT synaptosome and this results in the methylation of the histamine producing tele-methylhistamine. Tele-methylhistamine is then metabolized by MAO-A to produce tele-methylimidazoleacetaldehyde which activates the H2 receptor on the post synaptic nerve.

HMT is considered the rate-limiting enzyme in the metabolism of histamine in the nerve synapse since the histamine must be methylated before it can be metabolized by MAO-A. Any histamine that does not get methylated in the nerve synapse is picked up by the histamine reuptake transporter and delivered back to the H3 receptors on the presynaptic nerve. This activation of the H3 receptors inhibits the release of histamine into the nerve synapse resulting in a decrease in the metabolism of histamine into histamine H2. To illustrate this, FIG. 1 shows the release and regulation of the histamine metabolism in the nerve synapse.

In the treatment that is described in U.S. Pat. No. 6,277,402, histamine H2 levels are augmented directly by administration of a histamine H2 agonist. In the treatment described in U.S. Publication No. 20030113309, in turn, increased histamine H2 levels is achieved through manipulation of neuronal metabolism of the histamine H2 precursor compounds, by increasing the activity levels of histamine N-methyltransferase (HMT) or monoamine oxidase-A (MAO-A) or both; the MAO-A or MAO-A agonists increase the neuronal metabolism of histamine, producing the active histamine H2 agonist.

The inventor has discovered in the foregoing treatments that the effectiveness of an exogenously administered histamine diphosphate and/or an MAO-A agonist to metabolize neuronal histamine and produce optimal levels of histamine H2 is dependent on the level of activity of endogenous HMT. Since the level of activity of HMT is regulated by inheritance, it would be necessary to exogenously administer HMT to overcome an inherent deficiency of HMT activity. U.S. Pat. No. 4,769,322 to Eli Lilly & Co. describes a method of isolating and extracting HMT, but at present HMT is not commercially available. The present invention avoids this obstacle by methylating the histamine diphosphate in vitro prior to administration in vivo, so as to bypass the need for exogenous HMT administration or the need for increased endogenous HMT activity.

b. In Vitro Methylation of Histamine Diphosphate

Methylation is defined as the addition of methyl groups, and in biochemistry generally takes the form of exchange of a hydrogen atom for a methyl group. The scientist C.F. Code in 1971 demonstrated that histamine must first be methylated on the side chain to produce methyl derivatives that acted as H2 agonists resulting in increased gastric acid production. If methylation occurred on the histamine imidazole ring the H2 agonist effect was greatly diminished (S. J. Konturek, "Gastric Secretion—from Pavlov's Nervism to Popielski's Histamine as Direct Secretagogue of Oxyntic Glands", Journal of Physiology and Pharmacology 2003, 54, S3, pp. 43-68). In vivo, methylation of the side chain on histamine is catalyzed by the enzyme Histamine N-methyltransferase (HMT); regardless of whether HMT would be effective for in vitro methylation, the compound is for practical purposes presently unavailable.

As a practical solution, the inventor herein has found that thiols such as N-acetylcysteine and glutathione support and enhance the rate of in vitro methylation of histamine in the presence of a suitable methyl donor. In particular, in the present invention histamine diphosphate is methylated in vitro by combining the histamine diphosphate with a thiol such as N-acetylcysteine or glutathione with L-reduced glutathione generally being preferred, in an amount sufficient to facilitate the methylation of the histamine in the presence of a methyl donor. The methyl donor may be but not limited to betaine hydrochloride, S-adenosylmethionine (SAMe), and methionine, with betaine hydrochloride generally being preferred. The concentration of the preferred L-reduced glutathione is 1-10 gm per 15-30 gm of a methyl donor per 500 gm of histamine diphosphate.

The methylation is facilitated in an acid environment having a pH less than 3.0, with vigorous mixing under pressure to create a shearing force sufficient to facilitate the exchange of the methyl group to the histamine. For example, the treatment composition is suitably prepared by passing the mixture back-and-forth between a pair of syringes (suitably, 60 cc syringes), using strong, compressive strokes, or "swishes", in order to generate the necessary shearing action. Approximately 10-15 strokes of the mixture are normally required, depending in part on temperature, barometric pressure (fewer strokes generally being required at higher temperatures and pressures) and other factors. In so doing, the mixture develops a thick paste consistency, at which point it is immediately deposited in moulds and allowed to harden. The resulting material is suitably administered transdermally, although other forms of administration may be used. Transdermal administration by means of Karaya gum patch or disc is preferred in terms of effectiveness and efficiency; PLO gel may also be used, but has been found somewhat less effective, and more of the betaine hydrochloride (or other methyl donor) is needed to make up the necessary volume.

Using transdermal patches/discs, the treatment is suitably administered twice a day. Per disc, the amount of histamine diphosphate is preferably about 1.65 mg, and suitably in the range from about 0.2 mg to about 5.5-mg, and the amount of betaine hydrochloride is preferably about 5.3 mg, and suitably in the range from about 5.0 mg to about 100 mg. The L-reduced glutathione, in turn, is preferably included at about the ratio described above.

The following examples relate to actual practice of the invention described above in the alleviation of the symptoms of multiple sclerosis.

EXAMPLE 150 multiple sclerosis patients were receiving 1.65 mg of histamine diphosphate and 100 mg of a phosphodiesterase inhibitor, caffeine citrate, via transdermal patch as described in U.S. Pat. No. 6,277,402, the treatment being referred to by the trademark Prokarin™. The 150 patients reported a lessening of their MS symptoms while using the Prokarin™ treatment, such as a decrease in fatigue, improved balance, decreased pain, improved bowel and bladder control, improved mobility and dexterity and cognitive improvements.

However, when treatment was changed to the formulation of the present invention, employing L-reduced glutathione to facilitate methylation of the histamine in vitro, all 150 patients reported significantly greater improvements in their symptoms than had been experienced with the Prokarin™ treatment, despite the same amount of histamine diphosphate (1.65 mg) being administered in both formulations (along with 100 mg of caffeine citrate). The 150 patients not only reported significantly greater reduction in symptoms, but also fewer dosing issues arising from slight deviations from the standard dose.

The histamine diphosphate of the prior treatment also required a significantly slower titration of the dose (up to the standard 0.2 ml dose), in contrast to the histamine methylated in vitro in accordance with the present invention, in order to avoid H3 receptor stimulation due to excessive unmethylated histamine in the synapse; with the prior treatment this effect had on occasion been observed to cause an abrupt shutdown of histamine release and metabolism into the H2 agonist, resulting in a temporary worsening of symptoms and forcing the patients to restart titration of the dose.

As a further advantage, the in vitro methylation of the histamine in accordance with the present invention has resulted in the prepared formulation no longer requiring refrigeration, unlike the composition used for the prior Prokarin™ treatment.

It is to be recognized that various alterations, modifications, and/or additions may be introduced into the constructions and arrangements of parts described above without departing from the spirit or ambit of the present invention.

What is claimed is:

1. A method for treating multiple sclerosis, said method comprising the steps of:
   providing a selected histamine compound;
   methylating said selected histamine in vitro to form a methylated histamine compound; and
   administering to a patient an effective amount of said methylated histamine compound.

2. The method of claim 1, wherein said selected histamine compound is histamine diphosphate.

3. The method of claim 2, wherein the step of methylating said histamine compound in vitro comprises:
   combining said histamine diphosphate with at least one thiol compound in the presence of at least one methyl group donor compound.

4. The method of claim 3, wherein said at least one thiol compound is selected from the group consisting of:
   N-acetylcystiene;
   glutathiones;
   L-reduced glutathione; and
   combinations thereof.

5. The method of claim 4, wherein said methyl group donor compound is selected from the group consisting of:
   betaine hydrochloride;
   S-adenosylmethionine;
   methionine; and
   combinations thereof.

6. The method of claim 5, wherein the step of methylating said histamine compound in vitro further comprises the step of:
   vigorously mixing said histamine diphosphate, said thiol compound, and said methyl group donor compound under pressure in an acid environment so as to create a shearing force that facilitates exchange of a methyl group from said methyl group donor compound to said histamine diphosphate.

7. The method of claim 6, wherein said acid environment has a pH less than about 3.0.

8. The method of claim 5, wherein said thiol compound is L-reduced glutathione.

9. The method of claim 8, wherein said methyl group donor compound is betaine hydrochloride.

10. The method of claim 9, wherein said betaine hydrochloride is included in an amount in the range from about 15 gm to about 30 gm per each 500 gm of said histamine diphosphate, and said L-reduced glutathione is included in an amount in the range from about 1 gm to about 10 gm per each 15 gm-30 gm of said betaine hydrochloride.

11. The method of claim 10, wherein the step of methylating said histamine compound in vitro further comprises the step of:
    vigorously mixing said histamine diphosphate, said L-reduced glutathione, and said betaine hydrochloride under pressure in an acid environment so as to create a shearing force that facilitates exchange of a methyl group from said methyl group donor compound to said histamine diphosphate.

12. The method of claim 11, wherein said acid environment has a pH less than about 3.0.

13. The method of claim 10, wherein the step of administering an effective amount of said methylated histamine compound to a patient comprises:
    administering an effective amount of said methylated histamine compound to a patent by transdermal application.

14. The method of claim 13, wherein the step of administering an effective amount of said methylated histamine compound to a patient by transdermal application comprises:
    administering said methylated histamine compound by transdermal application twice daily, in an amount in the range from about 0.2 mg to about 5.5 mg per dose.

15. The method of claim 13, wherein the step of administering an effective amount of said methylated histamine compound to a patient by transdermal application comprises:
    administering said methylated histamine compound by transdermal application twice daily, in an amount of about 1.65 mg per dose.

* * * * *